United States Patent [19]

Magin et al.

[11] Patent Number: 5,679,620
[45] Date of Patent: Oct. 21, 1997

[54] HERBICIDAL AND PLANT GROWTH REGULANT COMPOSITIONS AND THEIR USE

[75] Inventors: Ralph W. Magin; Joe D. Sauer; John R. Maloney, all of Baton Rouge, La.

[73] Assignee: Albemarle Corporation, Richmond, Va.

[21] Appl. No.: 627,256

[22] Filed: Apr. 3, 1996

[51] Int. Cl.$^6$ .................. A01N 25/30; A01N 57/04
[52] U.S. Cl. .................. 504/206; 71/DIG. 1
[58] Field of Search .................. 504/206; 71/DIG. 1

[56] References Cited

U.S. PATENT DOCUMENTS

| | | | |
|---|---|---|---|
| 4,400,196 | 8/1983 | Albrecht et al. | 71/86 |
| 4,481,026 | 11/1984 | Prisbylla | 71/86 |
| 5,332,714 | 7/1994 | Albrecht et al. | 504/116 |

FOREIGN PATENT DOCUMENTS

| | | |
|---|---|---|
| 0617894 | 10/1994 | European Pat. Off. . |
| 9212637 | 8/1992 | WIPO . |
| 9600010 | 1/1996 | WIPO . |

OTHER PUBLICATIONS

Wyrill, III, J. B. and Burnside, O. C., —"Glyphosate Toxicity to Common Milkweed and Hemp Dogbane as Influenced by Surfactants", Weed Science, vol. 25 Issue 3 (May), 1977, pp. 275–287.

*Primary Examiner*—Richard L. Raymond
*Assistant Examiner*—Brian G. Bembenick
*Attorney, Agent, or Firm*—Philip M. Pippenger

[57] ABSTRACT

Glyphosate formulations which are effective even when employed at dosages below the dosage currently recommended for post-emergent herbicidal or plant growth regulant use are described. They are formulated as water solutions or powders or granules of (a) one or more agriculturally acceptable amine, alkali metal, alkylsulfonium, alkylphosphonium, sulfonylamine, and/or aminoguanidine salts of glyphosate as the only herbicide(s) used in the forming composition; and (b) one or more water-soluble particular types of aliphatic hydrocarbyl sulfonic acid or agriculturally acceptable salt or ester thereof as the only surfactants used in forming the composition. The hydrocarbyl group of the sulfonate is a saturated aliphatic group having in the range of about 10 to about 18 carbon atoms and is terminally substituted by the foregoing functionality.

16 Claims, No Drawings

HERBICIDAL AND PLANT GROWTH REGULANT COMPOSITIONS AND THEIR USE

TECHNICAL FIELD

This invention relates to glyphosate formulations which are highly effective even when employed at dosages below the dosage currently recommended for post-emergent herbicidal use against undesired vegetation.

BACKGROUND

Glyphosate, N-(phosphonomethyl)glycine, is a well-known widely used herbicide. It is generally employed in the form of an agriculturally acceptable salt.

In U.S. Pat. No. 5,116,401 to D. C. Young it is pointed out that although glyphosate is a very active, broad spectrum; systemic, relatively environmentally safe herbicide, its solubility in water at 25° C. is only 1.2 weight percent and many of its homologs and salts are only slightly soluble or are essentially insoluble in water and organic solvents. Thus in practice, formulations of glyphosate salts with other components to enhance its solubility and its effectiveness typically used.

Over the years a wide variety of substances, including surfactants, have been studied or proposed as adjuvants to enhance the effectiveness of glyphosate. For example, J. W. Kassebaum and H. C. Berk indicate in U.S. Pat. No. 5,317,003, that surfactants are usually employed to enhance the effectiveness of glyphosate when it is applied to the foliage of various plants, and that the most widely used surfactant in commercial compositions is an ethoxylated fatty amine. In addition, they refer to knowledge in the art that a particular surfactant used in an aqueous composition with a herbicide can enhance the effectiveness of the herbicide, whereas other surfactants have very little, if any, beneficial effect. They also note that some surfactants may exhibit antagonistic effects. As an example they cite the work of Wyrill and Burnside, *Weed Science*, Volume 25, (1977), pages 275-287 wherein, among other things, it was found that the surfactant ETHOQUAD 18/12 was relatively ineffective in enhancing phytotoxicity of glyphosate to hemp dogbane whereas in a separate experiment an analogous compound, ETHOQUAD 18/25, was one of the most effective surfactants tested.

Despite the extensive studies and efforts devoted to improving the performance of glyphosate, a need exists for a way of potentiating the effectiveness of glyphosate salts such as the amine, sodium, alkylsulfonium, alkylphosphonium, sulfonylamine, and aminoguanidine sails thereof by means of an environmentally friendly aqueous formulation made from a small number of ingredients, wherein the amounts of each of the components, including the glyphosate, can be kept very small, and wherein the resulting composition provides clearly observable herbicidal action, especially against undesired grasses, in a short period of time after application. It would be particularly desirable if this need could be fulfilled by use of readily available, cost-effective materials while at the same time avoiding the inclusion of polyvalent metal-containing and metalloid-containing components in the formulation.

This invention is deemed to fulfill the foregoing need in an effective and highly efficient manner.

THE INVENTION

This invention involves the discovery, inter alia, that certain alpha-olefin sulfonates are effective as adjuvants for increasing the phytotoxic effectiveness of glyphosate against a number of plant species, including crab grass and barnyard grass as well as certain broadleaf species, and that this effectiveness is clearly observable in a short period after application. Thus this invention makes it possible to achieve enhanced phytotoxic effectiveness in an aqueous solution formed from as few as two added ingredients, both of which are readily available in the marketplace. Moreover it is possible pursuant to this invention to employ the glyphosate herbicide in dosage levels substantially lower than currently recommended. Furthermore, the adjuvants used in the practice of this invention are in themselves environmentally friendly. And in addition, the formulation requires no polyvalent metal or metalloid components in its formation. Indeed the preferred compositions are devoid of metal and metalloid additive content, and most preferably contain only the elements C, H, O, N, P, and S. Moreover, the liquid concentrates are most preferably formed using deionized water.

The adjuvants used in forming the aqueous formulations of this invention are one or more water-soluble long chain alkane sulfonic acid, salt or ester (sometimes collectively referred to herein as "AOS") in which the long chain hydrocarbyl group is a linear or substantially linear alkyl group having in the range of about 10 to about 18 carbon atoms. By water-soluble is meant that the component is soluble to at least the extent of 1% by weight in deionized water at 25° C. When used in forming an aqueous concentrate of this invention, the adjuvant should have a water solubility of at least 5% by weight in deionized water at 25° C.

In accordance with one of its embodiments this invention provides a method of controlling vegetation by applying to plant foliage, preferably by spraying, a polyvalent metal-free and metalloid-free solution containing an effective herbicidal or plant growth regulant mount of a composition formed by intimately mixing the following ingredients with water:

(a) at least one agriculturally acceptable mine, alkali metal, alkylsulfonium, alkylphosphonium, sulfonylamine, and/ or aminoguanidine salt of glyphosate as the only herbicide or plant growth regulant used in forming the composition; and b) at least one water-soluble AOS in which the hydrocarbyl group is a linear or substantially linear saturated aliphatic group having in the range of about 10 to about 18 carbon atoms, as the only surfactant used in forming the composition.

Another embodiment of this invention is a polyvalent metal-free and metalloid-free herbicide or plant growth regulant composition formed by intimately mixing at least a herbicidal or plant growth regulant amount of ingredients (a) and (b) above with water, ingredient (a) being the only herbicide or plant growth regulant and ingredient (b) being the only surfactant used in forming the composition. Optionally, one or more substances that are not herbicides, or plant growth regulants, or surfactants, such as dyes, humectants, corrosion inhibitors, stickers, spreaders and thickeners, can be included as component (c) in these compositions.

Still another embodiment of this invention is a powder or granular herbicide or plant growth regulant formulation which comprises a mixture containing an effective herbicidal or plant growth regulant amount of a composition formed by intimately mixing together components (a) and (b), and optionally including one or more of (c) above. Such compositions can also be formed by evaporating to dryness (e.g., by spray drying, extrusion or pan granulation) a solution of components (a) and (b) above, and optionally (c) above. Application of the powder formulations to vegetation as foliar dusts for effecting control of the vegetation constitutes another embodiment of this invention.

It will be appreciated that to effect control of undesired plant vegetation pursuant to this invention, recourse may be had to herbicidal activity whereby undesired vegetation is killed and/or to plant growth regulant activity whereby the further growth of the vegetation is stunted, inhibited and/or slowed without actually killing all of the undesired vegetation treated with the composition.

The herbicidal (phytotoxic) and the plant growth regulant compositions of this invention include aqueous concentrates which can be shipped and stored until diluted with more water on site to produce the final solution for application to the foliage as by spraying. Likewise the herbicidal and the plant growth regulant compositions of this invention include the more dilute aqueous solutions for use in application to the foliage. These more dilute aqueous solutions are preferably formed simply by suitably diluting an aqueous concentrate of this invention with water (if a powder or granular concentrate) or with more water (if a liquid concentrate) to achieve the appropriate herbicidal or plant regulant dosage, but alternatively, can be formed on site by intimately mixing the separate ingredients or sub-combinations thereof with sufficient water on site to achieve the appropriate dosage. Use of the solid or liquid concentrates of this invention is preferable as it is a much simpler operation and minimizes the possibility of blending errors. Moreover, if desired, other components such as fertilizers, penetrants, spreaders, stickers, etc., can be introduced into the final solution at the time the concentrate is blended with water to form the diluted solution for application to the foliage.

Component (a)

The identities and methods for the preparation of the glyphosate ingredient of the formulation are well known and are reported in the literature. See for example, U.S. Pat. No. 3,799,758 to J. E. Franz which describes amine salts and alkali metal salts of glyphosate, and the production of glyphosate by such methods as the phosphonomethylation of glycine, the reaction of ethyl glycinate with formaldehyde and diethylphosphite, and the oxidation of the corresponding aminophosphinic compounds. Another method involves conducting a Mannich reaction with phosphorous acid and formaldehyde on iminodiacetic acid followed by controlled oxidation to N-(phosphonomethyl)glycine. Typically the amine of the glyphosate amine salts has a molecular weight of less than 300. A preferred amine salt of glyphosate is a salt formed with isopropyl amine. Of the alkali metal salts of glyphosate, sodium is the preferred cation. Inasmuch as glyphosate has more than one replaceable hydrogen atom, either or both of mono- and dialkali metal salts of glyphosate can be formed and used. The alkylsulfonium salts of glyphosate are described for example in U.S. Pat. No. 4,315,765 to G. B. Large, and analogous procedures can be used for producing alkylphosphonium salts. Of the alkylsulfonium and alkylphosphonium salts, the trimethylsulfonium salt of glyphosate is preferred. Sulfonylamine and aminoguanidine salts of glyphosate which are also suitable for use pursuant to this invention are disclosed in EP-A-0 088 180. The patent literature contains numerous additional references to various other methods for the production of glyphosate. See for example U.S. Pat. Nos. 4,851,159; 4,898,972; 4,937,376; 4,952,723; 5,061,820; and 5,072,033 to Fields Jr. et al.; U.S. Pat. No. 5,023,369 to Fields, Jr.; U.S. Pat. No. 4,853,159 to Riley et al; and U.S. Pat. No. 5,047,579 to Glowka et al., as well as relevant references cited in these patents. Fields, Jr. et al. U.S. Pat. No. 4,965,403 describes a process for producing the alkali metal salts of glyphosate. Aqueous solutions of glyphosate salts devoid of other adjuvants are commercially available from Monsanto Company and these solutions are suitable for use in forming the compositions of this invention.

Component (b)

This component in the form added to the water or aqueous solution is one or more water-soluble long chain aliphatic hydrocarbyl sulfonic acids or salts or esters in which the hydrocarbyl group is a saturated aliphatic group having in the range of about 10 to about 18 carbon atoms and is terminally substituted by sulfonic acid functionality such as the free sulfonic acid group, or an agriculturally acceptable derivative thereof such as a univalent sulfonic acid salt functionality or an agriculturally acceptable lower alkyl (e.g., up to about 4 carbon atoms) sulfonic acid ester group. Preferably the hydrocarbyl group is a straight chain primary or normal alkyl group bonded to the sulfonic acid moiety.

The free sulfonic acids, sulfonate salts, and esters can be represented by the following formula:

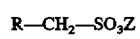

$$R\text{---}CH_2\text{---}SO_3Z$$

where R is an alkyl group having in the range of about 9 to about 17 carbon atoms, and Z is a hydrogen atom, a univalent cation (preferably an alkali metal cation such as a sodium or potassium cation, or an ammonium cation, or a quaternary ammonium cation, such as —$NH_3CH_3$, —$NH_3CH_2CH_3$, —$NH_3CH(CH_3)_2$, —$NH_3(CH_2)_3CH_3$, etc.) or an alkyl group having up to about 4 carbon atoms.

Of the above alpha-olefin sulfonate adjuvants of this invention, those in which the alkyl group contains about 12 to about 16 carbon atoms are preferred, and those in which the alkyl group contains about 12 to about 14 carbon atoms are most preferred. As noted above, this component can be a single compound or a combination or mixture of two or more compounds.

Methods for producing alpha-olefin sulfonates used as component b) in the practice of this invention are also well known and are reported in the literature. Typically they involve bisulfite addition to an alpha-olefin, but can also be formed by oxidation of lead mercaptides, or reaction of an alkyl halide with an alkali sulfite such as sodium sulfite or ammonium sulfite. Suitable compounds of the above formula are available as articles of commerce.

Table 1 sets forth general and preferred proportions for use in forming the water-soluble concentrate formulations of this invention. The percentages given in Table 1 are weight percentages, and represent weight percent of the total composition. The percentages for the amine, alkali metal, alkylsulfonium, alkylphosphonium, sulfonylamine, and/or aminoguanidine glyphosate salt ("Glyphosate Salt") used in the practice of this invention as given in Table 1 on an active ingredient basis and are in terms of glyphosate acid equivalent (i.e., the weight of the particular salt-forming portion of the product is excluded from the weight of the salt). Likewise the amount of any water associated with the salt as received is excluded from consideration as regards the percentages of the Glyphosate Salt shown in the table.

TABLE 1

| Ingredient | General Range, wt % | Preferred Range, wt % |
|---|---|---|
| (a) Glyphosate Salt | 0.1 to 65% | 18 to 65% |
| (b) AOS | 1 to 70% | 10 to 25% |
| Other Ingredient(s) | 0 to 20% | 0 to 5% |
| Water | Balance to 100% | Balance to 100% |

Table 2 sets forth the proportions which can be used in forming the powder or granular composition of this invention. As in Table 1, the percentages given in Table 2 are weight percentages on an active ingredient basis, and represent weight percent of the total composition. And as above, the percentages for the amine, alkali metal, alkylsulfonium, alkylphosphonium, sulfonylamine, and/or aminoguanidine glyphosate salt ("Glyphosate Salt") used in the practice of this invention as given in Table 2 are in terms of glyphosate acid equivalent.

TABLE 2

| Ingredient | General Range, wt % | Preferred Range, wt % |
|---|---|---|
| (a) Glyphosate Salt | 10 to 99% | 75 to 98% |
| (b) AOS | 1 to 90% | 2 to 25% |
| Other Ingredient(s) | 0 to 20% | 0 to 10% |

The diluted solutions for application to the plant foliage are typically formed prior to application using a tank mixer, spray tank or similar apparatus. The dosage level of the composition applied to the plant foliage will depend to some extent upon the plant species being treated, the extent of control desired, and the prevailing weather conditions. Generally speaking, however, the amount applied will be a herbicidal or growth regulant amount within the range of about 50 to about 1250 grams of glyphosate (on an acid equivalent basis, i.e., excluding the weight of the cationic salt associated therewith) per hectare. In terms of ounces avoirdupois per acre this range corresponds (on the same acid equivalent basis) to from about 0.7 to about 20 ounces of glyphosate per acre). In accordance with this invention it is preferred to employ a herbicidal or plant growth regulant amount (again on an acid equivalent basis) falling within the range of about 200 to about 830 grams of glyphosate per hectare which corresponds (on the same acid equivalent basis) to about 3 to about 12 ounces avoirdupois of glyphosate per acre), as this is generally sufficient to control most undesired plant species, is below the dosage currently recommended for herbicidal use of glyphosate formulations, and is thus more economical and environmentally friendly. On the basis of this disclosure and the new technology described herein, it is now possible to make departures from the foregoing ranges whenever such is deemed necessary or desirable in any given situation.

The following non-limiting Examples illustrate the practice and advantages of this invention.

EXAMPLES

A field test was conducted in which the effectiveness of compositions of this invention was compared with effectiveness of a standard recommended glyphosate formulation. The test formulations of this invention consisted of the aqueous solution made from (a) N-(phosphonomethyl) glycine isopropyl amine salt, (b) a mixture of alkane sulfonic acids having 14 and 16 carbon atoms in the molecule, and water. No other component or ingredient was employed in forming these test formulations.

The glyphosate used in forming these formulations was ROUND-UP® D-Pak from Monsanto, which is a 62.0% aqueous solution of the glyphosate isopropyl amine salt in water with no other component therein. The control formulation was an aqueous solution of N-(phosphonomethyl) glycine isopropyl amine salt and the commercial adjuvant INDUCE® (Helena Chemical Company) which, according to *A Guide to Agricultural Spray Adjuvants Used in the United States*, pby T. L. Harvey, 1992–93 Edition, Thomson Publications, Fresno, Calif., page 33 is alkyl polyoxyalkane ether, free fatty acids and IPA, which is an adjuvant currently recommended for use in glyphosate formulations. The control formulation was applied at the recommended dosage level of 15 fluid ounces of glyphosate (active ingredient basis) per acre (624 grams of glyphosate per hectare) whereas the formulations of this invention were applied at dosages of only 5 and 10 ounces of glyphosate (active ingredient basis) per acre (208 and 416 grams of glyphosate per hectare, respectively). All solutions contained one percent of the surfactant used.

All tests were conducted at the same experimental test site at the same time, and were performed with three replicate tests for each composition, using randomized plots. Each plot was 10 feet by 15 feet (ca. 3.1 meters by ca. 4.6 meters) in size. Single applications were made between 10:00 a.m. and 2:30 p.m. on the same calm, sunny day with a relative humidity reading of 75% and an air/soil temperature of 85° F. and 92° F. (ca. 30° C. and ca. 33° C.), respectively The application was made with a carbon dioxide pressurized back pack sprayer. The soil and leaf conditions were both dry at the time of application.

The population of weed species in the plots included the following:

1 to 3 square feet of morning glory (3–10 inches in height).

2 to 5 square feet of red weed (3–6 inches in height, with 3 to 6 leaves per plant).

3 to 5 square feet of sickle pod (3–7 inches in height, with 3 to 6 leaves per plant).

0 to 2 square feet of Hemp Sesbania (2–5 inches in height, with 3 to 5 leaves per plant).

1 to 4 square feet of barnyard grass and crab grass (3–5 inches in height, with 2 to 4 leaves per plant).

Observations of percentage of control were made at 7 days and 19 days after applications, and Table 3 summarize the results obtained in these tests. In Table 3 the results are shown in terms of their statistical significance within 95% confidence limits. Thus the symbol ⊕ signifies that the test formulation of this invention gave results that statistically were equivalent to results given by the control. In every case the glyphosate dosage level in the formulations of this invention was only a fraction (33% or 67%) of the glyphosate dosage level in the control formulation. The symbol ☉ signifies that statistically the result was only 1% below equivalence with the control, whereas the symbol ⊖ signifies that statistically the result was not equivalent to that of the control but nevertheless demonstrated plant growth regulant activity. Barnyard grass and crab grass are designated as "BYG and CG" in Table 3.

TABLE 3

Control of Plant Species Under Field Conditions

| Plant Species | Glyphosate Dosage, % of Control | Result, 7 Days | Result, 19 Days |
|---|---|---|---|
| Morning Glory | 33% | ⊕ | ⊕ |
| Morning Glory | 67% | ⊕ | ⊕ |
| Red Weed | 33% | ⊕ | ⊖ |
| Red Weed | 67% | ⊕ | ⊕ |
| Sickle Pod | 33% | ⊖ | ⊖ |
| Sickle Pod | 67% | ⊖ | ⊖ |
| Hemp Sesbania | 33% | ⊖ | ⊖ |
| Hemp Sesbania | 67% | ⊕ | ⊕ |
| BYG and CG | 33% | ⊕ | ⊖ |
| BYG and CG | 67% | ⊕ | ⊙ |

Optionally, one or more other substances can be employed in the formulations of this invention provided no such substance materially detracts from the effectiveness of the composition in combatting the particular plant species to be controlled by use of the formulation. By "materially" in this context is meant that in tests conducted by concurrent application under identical conditions and using identical dosages of one or the other of two (2) test formulations to a plant species in three (3) identical pairs of test plots (each pair consisting of a Case I plot and a Case II plot) in the same substantially uniform test site, where in Case I the formulation of this invention does not contain such additional substance(s) whereas in Case II the identical formulation does additionally contain such additional substance(s), there is a reduction in the average percentages of the plant species controlled in the three (3) Case II plots as compared to the average percentages of the plant species controlled in the three (3) Case I plots, and the arithmetic difference between these averages exceeds 10%. Such other substances that may be used if they do not materially detract from the effectiveness of the composition include dyes, pigments, humectants, corrosion inhibitors, thickeners, adhering agents (stickers), spreading agents, and like materials. Such other substances can be introduced into the formulation in any sequence relative to components (a) and (b) hereof, i.e., such materials can be added before, after or at the same time as either or both of components (a) and (b). In this connection, it will be recalled that the one or more glyphosate salts constitute (s) the only herbicide(s) or plant growth regulant(s) used in forming the compositions of this invention. Likewise one or more of the herein-described alpha-olefin sulfonate compounds constitute(s) the only surfactant(s) used in the practice of this invention. This ensures that the substantial benefits provided by this invention are realized in full.

The powder or granular formulations of this invention may be mixed with a finely-divided solid diluent such as talc, gypsum, Fuller's earth, kaolin, kieselguhr, bentonite, dolomite, calcium carbonate, and powdered magnesia. They may also be formulated as dispersible powders or grains, and in this case it is desirable to include a wetting agent to facilitate the dispersion of powder or grains in the liquid carrier. Additionally, formulations in the form of powders can be applied to vegetation as foliar dusts.

It is to be understood that the terms "ingredient" or "component" or "substance" as used anywhere in the specification or claims hereof, whether used in the singular or plural, are used in the sense that it is a substance employed in forming the powder or granular concentrate or aqueous solution, and thus at least prior to mixing with other ingredients or components and/or addition to an aqueous medium, the ingredient or component is in the chemical form specified. It matters not what chemical changes, transformations and/or reactions, if any, take place in the, mixture or aqueous medium itself as such changes, transformations and/or reactions are the natural result of bringing the specified ingredients or components together as solids or in aqueous medium.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A method of controlling vegetation which comprises applying to plant foliage a herbicidal or plant growth regulant amount of a composition formed by intimately mixing the following components with water:
   a) at least one agriculturally acceptable mine, alkali metal, alkylsulfonium, alkylphosphonium, sulfonylamine, and/ or aminoguanidine salt of glyphosate as the only herbicide (s) or plant growth regulant(s) used in forming the composition; and
   b) at least one water-soluble long chain aliphatic hydrocarbyl sulfonic acid or agriculturally acceptable salt or ester thereof in which the hydrocarbyl group is a saturated aliphatic group having in the range of about 10 to about 18 carbon atoms and is terminally substituted by the foregoing functionality, as the only surfactant(s) used in forming the composition:

the dosage at which said salt of glyphosate is being applied being equivalent on an active ingredient basis to no more than about 416 grams of glyphosate per hectare.

2. A method according to claim 1 wherein component a) thereof is an amine or alkylsulfonium salt of glyphosate.

3. A method according to claim 1 wherein component a) thereof is the isopropyl amine salt of glyphosate.

4. A method according to claim 1 wherein component b) thereof is at least one linear or substantially linear alkane sulfonic acid, salt or ester.

5. A method according to claim 1 wherein component b) thereof is a combination of at least two alkane sulfonic acids, salts or esters in which one alkane group has two more carbon atoms than the other.

6. A method according to claim 1 wherein component b) thereof consists essentially of a combination of two alkane sulfonic acids, salts or esters in which one alkane group has 14 carbon atoms and the other has 16 carbon atoms.

7. A method according to claim 1 wherein component a) thereof is an amine salt of glyphosate and wherein the aliphatic group of component b) thereof has in the range of about 12 to about 16 carbon atoms.

8. A method according to claim 1 wherein component a) thereof is the isopropyl amine salt of glyphosate, and wherein component b) thereof consists essentially of a combination of two alkane sulfonic acids, salts or esters in which one alkane group has 14 carbon atoms and the other has 16 carbon atoms.

9. A method of controlling vegetation which comprises applying to plant foliage a herbicidal or plant growth regulant amount of a polyvalent metal-free and. metalloid-free herbicide or plant growth regulant composition formed by intimately mixing: together the following ingredients:
   a) at least one agriculturally acceptable amine, alkali metal, alkylsulfonium, alkylphosphonium, sulfonylamine, or aminoguanidine salt of glyphosate as the only herbicide(s) or plant growth regulant(s) used in forming said composition;

b) at least one water-soluble long chain aliphatic hydrocarbyl sulfonic acid or agriculturally acceptable salt or ester thereof in which the hydrocarbyl group is a saturated aliphatic group having in the range of about 10 to about 18 carbon atoms and is terminally substituted by the foregoing functionality, as the only surfactant(s) used in forming the composition:

the dosage at which said salt of glyphosate is being applied being equivalent on an active ingredient basis to no more than about 416 grams of glyphosate per hectare.

10. A method according to claim 9 wherein said herbicide or plant growth regulant composition is in the form of a water solution, and wherein said composition is applied to the foliage as a spray.

11. A method according to claim 10 wherein said herbicide or plant growth regulant composition is in the form of a powder, and wherein said composition is applied to the foliage as a foliar dust.

12. A method according to claim 1 wherein said ingredient b) is a sodium or an ammonium salt of said sulfonic acid.

13. A method according to claim 8 wherein said ingredient b) is a sodium or an ammonium salt of said sulfonic acids.

14. A method according to claim 9 wherein said ingredient b) is a sodium or an ammonium salt of said sulfonic acid.

15. A method according to claim 10 wherein said ingredient b) is a sodium or an ammonium salt of said sulfonic acid.

16. A method according to claim 11 wherein said ingredient b) is a sodium or an ammonium salt of said sulfonic acid.

* * * * *